US010132766B2

(12) United States Patent
Grolier et al.

(10) Patent No.: US 10,132,766 B2
(45) Date of Patent: Nov. 20, 2018

(54) METHOD FOR THE ISOBARIC TRANSFER OF A FLUID FROM A DEPOSIT AND DEVICE FOR IMPLEMENTING SUCH A METHOD

(71) Applicants: INSTITUTO MEXICANO DEL PETROLEO, Mexico City (MX); UNIVERSITE BLAISE PASCAL—CLERMONT II, Clermont-Ferrand (FR)

(72) Inventors: Jean-Pierre Grolier, Clermont-Ferrand (FR); Stanislaw Randzio, Warsaw (PL); Marco Antonio Aquino-Olivos, Naucalpan (MX)

(73) Assignees: UNIVERSITE BLAISE PASCAL—CLERMONT II, Clermont-Ferrand (FR); INSTITUTO MEXICANO DEL PETROLEO, Mexico City (MX)

( * ) Notice: Subject to any disclaimer, the term of this patent is extended or adjusted under 35 U.S.C. 154(b) by 900 days.

(21) Appl. No.: 14/390,480

(22) PCT Filed: Apr. 8, 2013

(86) PCT No.: PCT/EP2013/057332
§ 371 (c)(1),
(2) Date: Oct. 3, 2014

(87) PCT Pub. No.: WO2013/150158
PCT Pub. Date: Oct. 10, 2013

(65) Prior Publication Data
US 2015/0092816 A1   Apr. 2, 2015

(30) Foreign Application Priority Data

Apr. 6, 2012   (FR) .................................... 12 53235

(51) Int. Cl.
*G01K 1/00*   (2006.01)
*G01K 17/00*   (2006.01)
(Continued)

(52) U.S. Cl.
CPC .......... *G01N 25/00* (2013.01); *E21B 49/083* (2013.01); *G01F 17/00* (2013.01); *G01L 9/00* (2013.01);
(Continued)

(58) Field of Classification Search
USPC ........................ 374/10, 143, 30, 54, 136, 31
See application file for complete search history.

(56) References Cited

U.S. PATENT DOCUMENTS

| 6,750,062 B1 * | 6/2004 | Randzio ................. G01N 25/02 422/51 |
| 7,031,740 B2 * | 4/2006 | Lundby ................. H04W 52/08 455/127.1 |

(Continued)

FOREIGN PATENT DOCUMENTS

WO   2012/025840   3/2012

OTHER PUBLICATIONS

International Search Report for PCT/EP2013/057332, dated May 6, 2013.

(Continued)

*Primary Examiner* — Mirellys Jagan
(74) *Attorney, Agent, or Firm* — Dickinson Wright PLLC (57) ABSTRACT

The invention relates to method for transferring under pressure a fluid extracted from the deposit by means of a sampling vessel (5) wherein the fluid sample is maintained at the reservoir pressure or extraction pressure, as well as to the method for determining at least one thermodynamic characteristic of this fluid, particularly a method for determining phase transition envelops. The invention also refers (Continued)

to a method combining the implementation of the scanning thansitiometry with spectroscopic or analytical techniques, eventually in the presence of a fluid in a supercritical state. The invention similarly refers to a device for implementation of the above-referred methods.

20 Claims, 3 Drawing Sheets

(51) Int. Cl.

| | | |
|---|---|---|
| *G01N 25/00* | (2006.01) | |
| *G01N 25/02* | (2006.01) | |
| *G01N 33/28* | (2006.01) | |
| *E21B 49/08* | (2006.01) | |
| *G01F 17/00* | (2006.01) | |
| *G01L 9/00* | (2006.01) | |
| *G01N 21/00* | (2006.01) | |
| *H01J 49/00* | (2006.01) | |

(52) U.S. Cl.
CPC .............. *G01N 21/00* (2013.01); *G01N 25/02* (2013.01); *G01N 33/2823* (2013.01); *H01J 49/0027* (2013.01)

(56) References Cited

U.S. PATENT DOCUMENTS

| | | | | |
|---|---|---|---|---|
| 9,291,585 | B2* | 3/2016 | Singh | ................. G01N 33/2823 |
| 2001/0030987 | A1* | 10/2001 | Plotnikov | .............. G01K 17/00 |
| | | | | 374/10 |
| 2011/0292382 | A1 | 12/2011 | Mostowfi et al. | |
| 2015/0211362 | A1* | 7/2015 | Rogers | .................... E21B 47/06 |
| | | | | 73/152.22 |

OTHER PUBLICATIONS

D. Bessières et al., "Apparatus for Simultaneous Determinaton of the Densities and Heat Capacities of Liquids and of Liquids with Dissolved Gas under an Extended Range of Pressure" (0.1-100 MPa), Meas. Sci. Technol. 11 (200), pp. N69-N72.
Notification of Transmission of International Search Report and Written Opinion dated May 6, 2013, which issued in PCT Patent Application No. PCT/EP2013/057332.
Ch. Stachowiak et al., "Transitiometric Investigation of Asphaltenic Fluids Under In-Well Pressure and Temperature Conditions," Energy & Fuels 2001, 15, © 2001 American Chemical Society, Published on Web Aug. 2, 2001, pp. 1033-1037.

* cited by examiner

METHOD FOR THE ISOBARIC TRANSFER OF A FLUID FROM A DEPOSIT AND DEVICE FOR IMPLEMENTING SUCH A METHOD

FIELD OF THE INVENTION

The invention refers to a method for transferring under pressure a fluid coming from a deposit of this fluid, at least from a sampling reservoir (5) where a sample of this fluid is maintained at the reservoir pressure (RP) and also a method for determining at least one thermodynamic characteristic of this fluid, particularly a method for determining a phase transition envelope. The fluid from the deposit is advantageously crude oil.

The invention also refers to a method combining scanning transitiometry and spectroscopic or analytical techniques eventually in presence of a fluid in a supercritical state.

The invention also refers to a device for implementing these methods.

BACKGROUND OF THE INVENTION

The hydrocarbons, particularly the crude oil comprise compounds named asphaltenes that participate into the heavy fraction oils. These asphaltenes have variable compositions but they are almost all soluble in toluene. It is generally considered that the asphaltenes precipitate in the presence of an alkane, for example in presence of a hexane, heptane and pentane. The percentage of asphaltenes in crude oil is variable and can be up to 56% by weight of oil.

The oil fluids have the particularity to precipitate in temperature conditions and pressure that are difficult to predict.

The asphaltenes are responsible of the precipitation of the crude oil and of the clogging of wells or pipes. This precipitate is made under pressure variation accompanying the exit of the crude oil from the deposit up to the surface and during the transfer to the surface of the oil, even under pressure.

The knowledge of the temperature and the pressure, from which the precipitation of the asphaltene phase occurs, is important for optimizing oil extraction.

Also, the determination of the bubble pressure, i.e. the pressure, from which the first gas bubble appears under the effect of pressure decrease, when the oil passes from the liquid phase to the gas phase, it allows optimizing the oil extraction. In order to determine these parameters, there are standardized methods defined by the ASTN D.3279 and ASTM D.4124 rules.

The titration of the oil fluids, particularly the determination of the title in asphaltene, may prove to be essential, particularly for samples maintained in the deposit conditions (live oils) in relation to the samples for which these conditions were not maintained (dead oils). This titration can precisely allow the determination of the quantity of asphaltenes in risk of precipitating.

Otherwise, from the patent application FR-2 771 818, we know a method and a device allowing determining the thermodynamic characteristics of a polymer, for example the thermophysical properties and the phase transition envelope.

Nevertheless, with such a device, the measurements are made with a sample that was introduced in a device at a pressure that is not always representative of the origin pressure of the sample.

Furthermore, for a crude oil sample, if the pressure, at which the measurement is made, is less or equal to the bubble pressure, at least a partial precipitation of asphaltenes occurs. Thereby, the method described in the patent application FR-2 771 818 does not allow a generally reliable measurement.

Stachowak et al. (Transitiometric investigation of asphaltenic fluids under in-well pressure and temperature conditions, Energy and Fuels, vol. 15, September 2001, pages 1033-1037) describes a study on oil fluids in pressure and temperature conditions of deposit wells.

Nevertheless, the method described does not allow a precise measurement of the volume of the displaced mercury. The results of this method are distorted.

However, Bessières et al. (Design note: apparatus for simultaneous determination of the densities and heat capacities of liquids and of liquids with dissolved gas under an extended range of pressure (0.1-100 MPa, Measurement Science and Technology, vol. 11, May 1, 2000, pages N69-N72) describe the transfer of a fluid containing a certain quantity of gas at least from a pneumatic pump in order to carry out measurements by means of calorimetry.

Or, it is necessary to be able to carry out representative measurements of the crude oil sample behavior; both in the oil deposit and after the extraction of the sample and even after the variation of pressure and temperature that suffers the oil sample after its extraction.

SUMMARY OF THE INVENTION

In order to obtain representative thermodynamic characteristics, particularly the bubble pressure and phase transition envelope of a crude oil sample, it is necessary to make measurements in a determined volume of the sample, whose initial pressure is controlled, the sampling pressure, as well as the sampling temperature during the whole process of measurement. The thermodynamic characteristic of such a sampling, whose control is essential, is generally the pressure.

In order to carry out extraction of the crude oil, there are various vessels including sampling bottles under pressure, called HPB bottles, for example, those used by the oil industry.

During the measurements, these crude oil samples are set at a pressure and a temperature where it can be guaranteed that they reliably reproduce the initial conditions of the sampling.

After modifying the reservoir conditions (RC), it is possible that the sample already passed through a modification of certain thermodynamic characteristics, even the initiation of precipitation.

However, after the insertion of the given volume of the sample in a measurement device, the pressure of the sample remaining in the sampling reservoir can be modified, that affects the subsequent measurements of this sample.

The implementation of the known techniques does not allow preserving the initial pressure of the sample during its transfer between the HPB bottle and the measurement device.

Based on the above, certain thermodynamic characteristics cannot be representatively determined from the behavior of the oil after the deposit till the surface.

The methods and devices according to the invention allow bringing solution to all or part of the problems found during the implementation of the known methods and devices.

Therefore, the invention provides an easy, rapid and reliable method of implementation, allowing the determination of the representative characteristics of the thermodynamic behavior of the asphaltene phases of a hydrocarbon in extraction conditions.

During the extraction and its transportation to different treatment areas, the hydrocarbons, particularly the crude oil, will evolve the pressure and temperature to which it was initially submitted.

This evolution is generally translated by a lower joint of pressure and temperature. In other terms, the initially liquid state, viscous or pasty, of the crude oil, is modified. Certain compounds of crude oil can precipitate and can disrupt the oil flow. The precipitation can lead to the obstruction of the installations, particularly wells and pipelines.

The composition of crude oil is variable from a deposit to another but similarly from a well to another even in the same deposit. Furthermore, taking into account the depth of different wells from the same deposit, the pressures and temperatures found vary according to the sampling point of the oil in a given well.

The heavy fraction of the crude oils is formed particularly of aromatic molecules, regrouped under the name of asphaltenes. The pressure and temperature conditions where the phase change occurs, solid/liquid or liquid/gas, the asphaltenes allow determining the thermodynamic work, pressure and temperature characteristics that must be carried out during extraction and transportation of hydrocarbons.

It is also possible to maintain the oil in liquid form during the extraction and after the precipitation of the asphaltene phase before proceeding to the transfer of the oil to the oil treatment and refinement installations.

It is also important to determine the bubble pressure of crude oil, i.e. the pressure when the first steam vapor appears when the crude oil suffers a pressure decrease. Actually, the presence of hydrocarbon steam in the well or in the pipelines, impact the oil transfer.

Thus, for the determination of thermodynamic characteristics of a hydrocarbon, particularly crude oil, it is essential to be able to reproduce as closely as possible the initial conditions in which the hydrocarbon is found. These initial conditions design all conditions, for example temperature and pressure, found in the extraction area.

These initial conditions, called reservoir conditions (RC) must be known for being able to determine the evolution of certain thermodynamic characteristics of asphaltene crude oil.

DETAILED DESCRIPTION OF THE INVENTION

In this regard, the invention provide a method for transferring under pressure a fluid extracted from a fluid deposit, at least from a sampling vessel (5) in which the sample is maintained at reservoir pressure (RP) or sampling pressure and comprises the following steps:

a) measure, in the absence of the contact with the sample, the pressure of the sample maintained at reservoir pressure (RP) in the sampling vessel (5);

b) connect the sampling vessel (5), maintained closed and at the reservoir pressure of a measuring device;

c) fill in the measuring device with a second liquid fluid, neutral versus the sample, with a known density and superior to the density of the fluid from the deposit;

d) increase the pressure in the measuring device and the pressure of the second neutral liquid fluid containing it, up to a pressure equal to the pressure of the sample of the fluid from the deposit determined during the step (a);

e) increase the pressure of the fluid sample from the deposit contained in the sampling vessel (5) to a pressure superior of the pressure of the second neutral liquid fluid contained in the measuring device;

f) transfer simultaneously, all or part, of the fluid sample from the deposit from the sampling vessel (5) to a measuring cell (2), by balancing the pressures of the sampling vessel (5) and the measuring cell (2); and a volume equivalent to the second neutral liquid fluid, of the measuring cell (2) to the sampling vessel (5);

g) after disconnecting the sampling vessel (5), measure the density of the second liquid, neutral fluid transferred into the sampling vessel (5), to a constant pressure in the absence of the contact with the sample of the fluid from the deposit;

h) calculate the volume of the sample of the fluid from the deposit, displaced and introduced in the measuring cell.

Advantageously, the transfer method according to the invention refers to a fluid from the deposit made of crude oil comprising an asphaltene phase.

The transfer method according to the invention can be implemented for the transfer of any type of hydrocarbons particularly containing waxes, resins or gas.

Another advantageous way, after implementing a transfer method according to the invention, particularly during one or another step (a) to (h), the sample of the fluid from the deposit present in the sampling vessel (5) or in the measuring cell (2) is heated and maintained at the reservoir temperature.

Preferably, during the step (a) of the transfer method according to the invention, the pressure of the sample of the fluid from the deposit contained in the sampling vessel (5) increases up to a pressure of 5 MPa to 7 MPA to the pressure of the second neutral fluid contained in the measuring device.

It is also preferable, during the implementation of the transfer method according to the invention, particularly during the step (e), the sample of the fluid from the deposit to be maintained at a pressure superior or equal to the bubble pressure of this fluid.

Also preferably, the transfer method according to the invention comprises the heating of the fluid sample from the deposit in the sampling vessel (5) or in the measuring cell (2) at the reservoir temperature (RT) of the deposit.

Before the step (e) or before the step (d) and during the previous step, the measuring cell is heated and maintained at the reservoir temperature of the fluid that is the temperature of the extraction of the sample.

More preferably, the transfer method according to the invention allows maintaining the fluid of the reservoir pressure in the sampling vessel (5) after disconnecting this last measuring device. It is also possible to proceed to other measurements.

Before implementing the transfer method according to the invention, it is possible to advantageously verify the stability of maintenance of pressure in the measuring device, for example injecting nitrogen in order to verify the absence of leakage.

The transfer method according to the invention allows advantageously maintaining constant the initial pressure of the sample of fluid in order to determine the thermodynamic characteristics taking into account the volume of this sample of fluid.

Also, the invention provides a method for determining at least a thermodynamic characteristic of a fluid from a deposit comprising the transfer of one sample of fluid from the deposit according to the transfer method according to the invention followed by the step (i) consisting of determining at least a thermodynamic characteristic of the fluid from the deposit at least of a measuring cell (2) adapted to carry out the determination of at least such a thermodynamic characteristic.

The method for determining at least a thermodynamic characteristic according to the invention comprising the following steps:

a) measure, in the absence of the contact with the sample, the pressure of the sample maintained at the reservoir pressure (RP) in the sampling vessel (5);

b) connect the sampling vessel (5) maintained closed and at the pressure of the reservoir, to a measuring device;

c) fill the measuring device with a second neutral fluid vis-à-vis to the sample, with known density and superior to the fluid from the deposit;

d) increase the pressure in the measuring device and the pressure of the second neutral liquid fluid containing it, up to a pressure equal to the pressure of the sample of the fluid from the deposit determined during the step (a);

e) increase the pressure of the fluid sample from the deposit contained in the sampling vessel (5) to a pressure superior of the pressure of the second neutral liquid fluid contained in the measuring device;

f) transfer simultaneously, all or part, of the fluid sample from the deposit to the sampling vessel (5) to a measuring cell (2), by balancing the pressures of the sampling vessel (5) and the measuring cell (2); and a volume equivalent to the second neutral liquid fluid, of the measuring cell (2) to the sampling vessel (5);

g) after disconnecting the sampling vessel (5), measure the density of the second liquid, neutral fluid transferred into the sampling vessel (5), to a constant pressure in the absence of the contact with the sample of the fluid from the deposit;

h) calculate the volume of the sample of the fluid from the deposit displaced and introduced in the measuring cell;

i) determine at least a thermodynamic characteristic of the fluid from the deposit within a measurement cell (2) adapted to carry out the determination of at least one thermodynamic characteristic.

The advantageous or preferred characteristics of the transfer method according to the invention equally defined the advantageous and preferred conditions of the determination method of at least a thermodynamic characteristic according to the invention.

Advantageously, the method of determination according to the invention can be implemented to determine at least one thermodynamic characteristic selected between a thermophysical characteristic and a thermomechanic characteristic, a phase transition envelope, the bubble pressure, titration, compressibility, thermal expansion.

During the implementation of the determination method according to the invention, it is possible to determine a thermodynamic characteristic by variation of a first parameter selected between pressure (P), temperature (T) or volume (V), based on a second parameter, maintaining constant the third parameter.

Advantageously, the method of determination of at least one thermodynamic characteristic according to the invention allows determining, separately or simultaneously, the phase transition envelope or bubble pressure of the asphaltene phase of the crude oil.

The method for determining a thermodynamic characteristic according to the invention allows to particularly determining the conditions of precipitation of asphaltenes of a crude oil sample, based on pressure and temperature. This method allows equally determining the evolution of the bubble pressure.

It is possible to represent, particularly for a crude oil sample, the evolution of the pressure according to the temperature maintaining constant the volume of the sample; the reservoir conditions (RC) were previously measured.

It is also possible to determine a high value (HV) and a low value (LV) of the pressure based on temperature and that correspond to pressures to which the precipitation of asphaltenes is possible. These values (HV) and (LV) of the pressure define the asphaltenes phase envelope of the tested oil sample.

It is also possible to determine the value of the bubble pressure (B) of the crude oil sample.

The transfer method according to the invention or the method for determination according to the invention can be similarly implement one or various elements selected among probes, optical fibers or other means for connecting the spectroscopic measurement or analytical sensors such as infrared spectroscopic sensors, ultra-violet spectroscopic sensors or mass spectroscopy. These additional elements can be combined with miniature capillary or micro capillaries allowing the injection of at least a fluid, for example the injection of an alkane (particularly pentane, hexane or heptane) or the injection of at least a fluid in its supercritical state, for example the injection of nitrogen in the supercritical state, $CO_2$ to the supercritical state or methane in the supercritical state.

A stirring system can equally be implemented in the measuring cell.

Said modified methods according to the invention have additional advantages, particularly those that allow the determination of thermodynamic characteristics of crude oils, the determination of the precipitation threshold/or flocculation of heavy compounds (particularly asphaltenes, resins or waxes), the quantification of the concentration of heavy compounds, the determination of the precipitating agents or flocculation (particularly gas or fluids in supercritical state), the kinetics follow up of the phenomenon observed by a simultaneous, calorimetric, spectroscopic or analytical double determination. Furthermore the use of the spectroscopic or analytical analyses provides access to the chemical nature of species presented in the transitiometric measuring cell, the implementation of a chemical reactor.

Furthermore the invention provides method for coupling transitiometry and at least one spectroscopic or analytical technique.

After implementation of these methods, it is possible to cause asphaltene precipitation within the crude oil sample. The elemental asphaltene particles can be added and give birth to the aggregates that flocculate. This phenomenon can be started by addition, particularly by injection, in the oil fluid being an alkane (pentane, hexane or heptane), even a gas (methane, nitrogen or carbon dioxide in a super critical state or even of another fluid in a super critical state).

The presence of at least an optical fiber introduced in the transitiometric measurement cell allow simultaneously following the thermal effect due to the physicochemical phenomenon and precipitation, also the changes of optical density of the beam transmitted to the medium. The simultaneous registration of the calorimetric sign (thermogram) and of the optical sign (spectrogram) evidences the consistency of these two signals and can allow showing two effects, calorimetric and spectroscopic, which are concurrent.

The method according to the invention allows accessing the complete information, quantitative and qualitative, as thermodynamic and kinetic. These methods can be coupled to experimentally study the behavior of the oil fluids of any nature allowing constituting an important database for a better knowledge of the fluids from the deposit and optimization of its exploitation.

The invention similarly refers to a device useful to implement the transfer method under pressure of a fluid from a deposit as well as for the implementation of the method for determining al least one thermodynamic characteristic of this fluid. Also, the invention provides a transfer device at reservoir pressure (RP) of a fluid sample extracted from a deposit and the determination of at least a thermodynamic characteristic of the fluid comprising:

- a measurement device of thermodynamic characteristic comprising at least a measuring cell (2), a reference cell (3), heating device and device for increasing o decreasing the pressure in the measuring (2) and reference cells (3);
- a sample removable vessel (5) comprising a compression liquid and placed at an inferior height of the measuring cell (2);
- a first reservoir (R1) of a liquid compression fluid and neutral vis-à-vis to the fluid sample from the deposit to be transferred;
- devices for increasing pressure in the sampling vessel (5);
- devices for equilibrating pressures in the measuring cell (2) and in the sampling vessel (5);
- a second reservoir (R2) of a liquid and neutral fluid vis-a-vis to the fluid sample from the deposit transferred and placed to a height superior to the first reservoir (R1) of the compressing fluid;
- ducts connecting the sampling vessel (5), the reservoirs (R1, R2) and the measuring cell (2).

The sampling vessel (5) of the device according to the invention can be cylindrical and can have a circular base.

The device according to the invention advantageously comprises a heating device of the sampling vessel (5).

Advantageously, the sampling vessel (5) is a high-pressure bottle (HPB). The high-pressure bottles are used in the oil extraction industry in order to carry out the in situ extraction. In a known matter, the high-pressure bottles can be adapted based on specific needs of extractions. They allow maintaining the fluid sample extracted from the deposit to an extraction pressure or reservoir pressure (RP).

The device according to the invention can be equally comprise a sampling vessel (5) comprising
- a compartment (6) connected by a duct (21) to the measurement cell (2) and that can receive the fluid sample from the deposit to be transferred;
- a compartment (7) connected by a duct (8) to a weighing member (10) and that can receive the compression liquid.

Preferably, the sampling vessel (5) comprises two compartments (6, 7) divided by a mobile wall (54) in translation along the longitudinal axis (X) or the sampling vessel (5).

More preferably, the sampling vessel (5) comprises a first compartment (6) provided with an outlet (51) connected by a duct (21) to the measuring cell (2) and a second compartment (7) provided with an outlet (50) connected by a duct (8) to a weighing member (10).

The two compartments (6, 7) of the sampling vessel (5) can eventually communicate in the absence of the separation wall.

Similarly, the device according to the invention can contain a weighing member (10), preferably a balance, connected by a duct (8) only to the compartment (7) of the compression liquid of the sampling vessel (5).

The member (10) or the duct (8) that connects the measuring device can be equipped with sensors (14), for example pressure, temperature or other parameters measuring sensors.

Preferably more advantageous, the device according to the invention uses a neutral fluid and a compression fluid that are identical; preferably the two fluids are identical and are made of mercury.

Indeed, the mercury is a neutral fluid compared with oil and has a higher density to that least. It is advantageously selected as a neutral fluid and compression fluid.

However, we can use another liquid neutral fluid with similar characteristics, particularly referring to its density.

The device according to the invention can similarly comprise a measuring cell (2) that is a transitiometer, particularly scanning transitiometry.

It can also comprise a titration means (35) of the fluid from the deposit, preferably a titration vial, and the ducts (37, 38) connecting this titration device to the measuring device.

The device according to the invention can equally comprise one or various elements selected between probes, optical fibers and other means for connecting the spectroscopic measuring or analytical detector such as infrared spectroscopic detectors, ultra-violet spectroscopy of mass spectroscopy.

These additional elements can be combined with miniature capillary or micro capillaries allowing the injection of at least a fluid, for example the injection of an alkane (particularly pentane, hexane or heptane) or the injection of at least a fluid in its supercritical state, for example the injection of nitrogen in supercritical state, $CO_2$ in supercritical state or methane in supercritical state. A stirring system can equally be implemented in the measuring cell.

The different elements of the device according to the invention, and particularly the measuring cell (2), for example a transitiometer, are carried out of a material resisting to high pressures and temperatures close to those found in the oil extraction. This material is neutral compared with the fluids that it receives. Advantageously, it is a stainless steel.

The following examples are the illustration of different devices according to the invention and also the implementation of the methods according to the invention for transferring a fluid and for determining a thermodynamic characteristic of said fluid.

These examples are not limiting the scope of protection of the present invention but allow bringing an illustration and highlighting various advantages of this invention.

Example 1: Device and Method for Determining the Phase Transition Envelop and Bubble Pressure of the Crude Oil Samples Containing Asphaltenes—FIG. 1

The determination of the phase transition envelope and bubble pressure of the crude oil samples containing asphaltenes can be carried out wherever gravimetric densities and colors are (defined according to the API norms—American Petroleum Institute) of the crude oil samples.

The crude oil samples coming from a well located in the Mexican Gulf have been used without representing any limitation. The measurements have been carried out in the deposit of origin of the oil sample.

The origin well of the sample is located in the Mexican Gulf, at a depth from 80 m to 8200 m, at a pressure oscillating from 8.3 MPa (1200 psi) to 55.2 MPa (8000 psi) and a temperature from 80° C. to 170° C.

The crude oil sample tested at about 0.5% by weight of asphaltenes, 6.3% by weight of resins and 60.5% by weight of saturated hydrocarbons. Its density is of 0.68 and its molecular weight is of 258.5.

The temperature of the reservoir that is the temperature prevailing in the deposit at the sampling point is of 154° C. The reservoir pressure that is the pressure prevailing in the deposit at the sampling point is of 29.7 MPa.

The measurements were done by means of a measuring cell as the one described in the patent applications FR-A-2 771 8181 and FR-A-2 679 650.

The method of determination essentially consists of generating a transition or change of the state of a compound in view of determining different thermodynamic characteristics. This change of state is carried out by a controlled measure, in defined ranges of temperature and pressure, of the variation of a first parameter based on the second parameter, maintaining a third parameter constant, the three parameters were selected between pressure, temperature or volume.

The variation of each parameter and the calorimetric signal related are registered and allow, after treatment, to determine the characteristics or thermodynamic derivatives of the sample.

This method of transitiometry implements the scanning transitiometry provided by BGR TECH society (Warsaw, Poland). This device allows carrying out measurements at a pressure from 0.1 to 400 MPa, i.e. up to 700 MPA, and in a range of temperatures from 173 K to 673 K, and for sample volume comprised between 0.3 and 4 mL. An acquisition module and data treatment allows the treatment of collected thermodynamic data.

The transitiometer comprises an insulated enclosure (1) equipped with a heating device related to a cooling device (not represented in FIGS. 1 and 2) that allows assuring a temperature maintenance of a measuring cell (2) and a reference cell (3). Each of these cells (2, 3) is adapted to receive a particular volume of a sample or a neutral liquid fluid. The pressure and the temperature prevailing in each cell (2, 3) can be modified together or independently.

Figure 1:
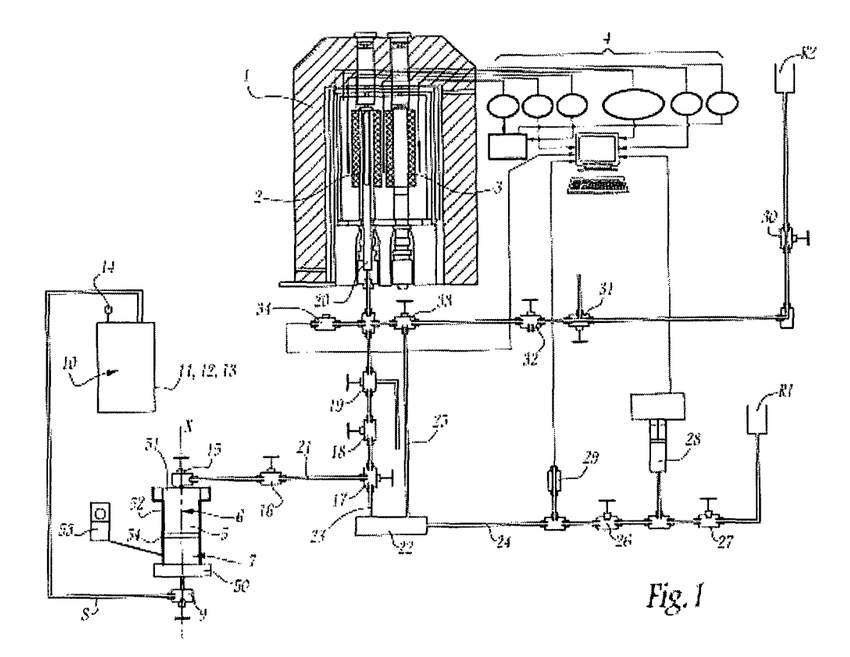
FIG. 1 is a schematic representation of a device according to the invention.
Figure 2:
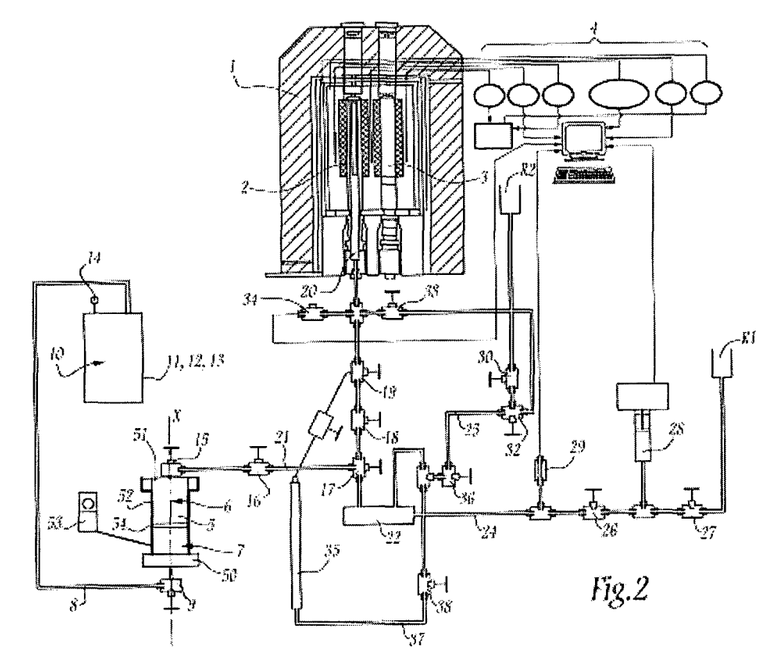
FIG. 2 is a schematic representation of another device according to the invention.
Figure 3:
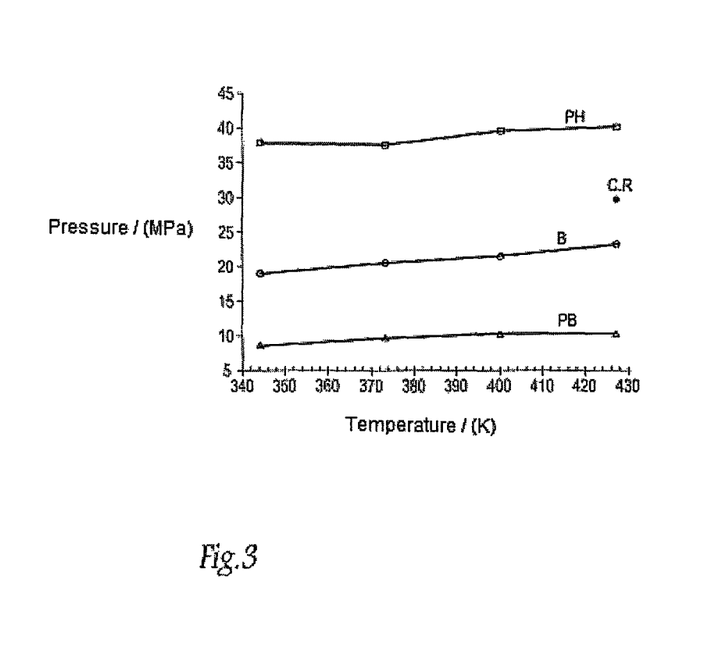
FIG. 3 represents, for a sample of crude oil, the evolution of pressure according to the temperature maintaining constant the sample volume.

The reference cell (3) is filled in with a neutral liquid vis-à-vis the sample tested that is made of mercury. The mercury is a neutral liquid without chemical or physical interaction with the hydrocarbons. There is a density superior to those of hydrocarbons. The mercury forms a neutral reference liquid, not miscible with the sample and can be compressed and heated.

The measuring cell (2) is adapted to receive a given volume of a crude oil sample. This volume is comprised between 0.3 and 4 mL.

When it contains a sample, the cell (2) can be placed under pressure and maintained at a certain temperature.

The cells (2, 3) have a cylindrical form with a circular base. An extremity (20) of the measuring cell (2) is connected to a duct circuit provided with sluice gates. All the elements of the transitiometer and particularly of the measuring device are made from stainless steel resisting high pressure and temperature close to those actually found in the oil extraction. The material is neutral compared with the fluids it receives.

The ducts have a thickness superior to its useful diameter. Based on the above, these ducts are treated as capillary tubes. The accessories are provided on the ducts circuit connecting different elements. These accessories are fixedly mounted or immobile. We speak of temperature sensors, pressure sensors or pumps. The sensors allow collecting data related to device operation and to manage the scanning temperature, through an acquisition module and data treatment (4).

The devices of FIG. 1 or 2 equally comprise two reservoirs (R1, R2) destined to respectively receive a compression liquid and a neutral liquid. This liquid is mercury for both liquids.

The location of the reservoirs (R1, R2) is adapted to the length and the configuration of the ducts circuit. The reservoir (R2) is placed at a height superior to that of the reservoir (R1).

The transfer device of the sample according to the invention comprises a sampling vessel (5) called high-pressure bottle or HPB that is cylindrical and have a circular base. It is provided with exits (50, 51) to each end and at least an entrance (52) to a sensor (53), for example a temperature sensor or a pressure sensor. The used bottles (5) can generally contain between 250 mL and 750 mL of the hydrocarbon sample.

The used bottle (5) allows the extraction of the crude oil sample in a known way. The useful volume of the bottle (5) is divided in two compartments (6, 7). This separation is carried out by a mobile wall (54) that is a mobile membrane in translation according to the parallel direction to an X longitudinal axe of the bottle (5). This wall (54) assures the tight separation between the first compartment (6), defining a sample reception volume and the second compartment (7) defining a reception volume of a compression fluid. The compression fluid is synthetic oil or can also be mercury.

The mobile wall (54) can be displaced under the effect of pressure exercised by the sample contained in the compartment (6) until the point where the pressures of two compartments (6, 7) are equilibrated and that the compression fluid contained in the compartment (7) is found at the same pressure as the sample in the compartment (6).

The compartments (6, 7) are partially delimited by the bottle ends (5) provided with exits respectively (51, 50).

When the exit (50) is open, the displacement of the mobile wall (54) induces a displacement of the compression fluid out of the bottle (5).

When the exit (50) is closed, the displacement of the mobile wall (54) induces a compression of a compression fluid.

In the pressure sensor (53) placed at the level of the compartment (7), the pressure of the compression fluid is measured, that is identical to the sample pressure.

It is possible to determine the initial pressure of the sample without modification and in absence of the direct contact with the sample.

A duct (8) provided of at least one sluice gate (9) connects the bottle (5), from the receiving compartment (7) of compression fluid to a weighing member (10).

The weighing member (10) comprises a balance, known per se, having a pressure of 0.1 mg. This balance allows measuring the density of the compression fluid that is found in the vessel of a weighing container adapted to weigh a liquid. This balance is located in a closed chamber, provided with sluice gates (11, 12, 13) allowing controlling the displacement of the compression liquid from the compartment (7) of the bottle (5) to the weighing member (10). Also, the weighing member (10) can be isolated from the bottle (5). It is equally possible to allow the circulation of the compression liquid between these two elements. A pump can assist this circulation.

Alternatively, the bottle (5) can be disconnected from the device in order to allow weighing the compression liquid.

The chamber in which the weighing member is found (10) allows assuring the temperature and the maintenance of temperature in the weighing member (10) without the contact with the compression liquid and maintenance of the compression liquid pressure. Consequently, the compression liquid pressure does not vary between the compartment (7) of the bottle (5) and the weighing member (10).

The bottle (5) is placed in order to begin the displacement by gravity of the sample and afterwards (5) to the measuring cell (2) when the sluice gates are open and the measuring device has the same pressure. Preferably, the bottle (5) is placed at a height inferior to that of the measuring cell (2), particularly at a height inferior to that of transitiometer height.

Since the weighing member (10) is not connected to the compartment (6) of the bottle (5) containing a sample, the opening of the sluice gates (9, 11, 12, 13) generated an equilibrium of the sample pressures and the compression liquid respectively present in the compartments (6) for the sample and in the compartment (7) and in the weighing member (10) for the compression liquid.

The member (10) is provided with sensors (14), for example pressure sensors, temperature sensor or other parameters.

From the exit (51) of the compartment (6) of the sample, the bottle (5) is equally connected to a measuring cell (2) that is a scanning transitiometer. The sluice gates (15, 16, 7, 18, 19) provided on the duct (21) allow its connection assuring that there is no communication between the interior part of the bottle (5) and the interior part of the transitiometer (2), meanwhile (15, 16, 17, 18, 15) is closed.

The rest of the circuit of the measuring device comprises an expansion chamber (22) connected to the measuring cell (2) by means of the ducts (21, 23) and a reservoir (R1) of neutral liquid by a duct (24) as well as a reservoir (R2) by another duct (25).

Also, the chamber (22) allows regulating the debits and pressures of the liquid circulating in different ducts (21, 23, 24, 25) of the circuit.

The duct (24) is provided with at least two sluice gates (26, 27) placed at one side and the other of the pump (28) and close to the reservoir (R1). The pump (28) and the pressure sensor (29) are connected to the module (4).

The duct (25) equally comprises sluice gates (20, 31, 32, 33).

A sluice gate (31) is provided with a free exit allowing taking out the liquid present in the duct (25), meanwhile two sluice gates (30, 32) are placed on one part and the other of the sluice gate (31) and close to the reservoir (R2).

The three-way sluice gate (33) is connected to the duct end (23) and close to the measuring cell (2). From the reservoir (R2), the three-way sluice gate (33) allows injecting a neutral liquid directly in the circuit, independent of the chamber (22). The three-way sluice gate (33) can equally serve for isolating the measuring cell (2).

A sensor (34) connected to the module (4) is present in the duct (23), between the sluice gate (33) and the end (20) of the measuring cell (2).

The devices shown in FIGS. 1 and 2 have a mobile wall (54) but in an alternative embodiment (not represented), when the selected compression liquid is identical to the neutral liquid, for example mercury, neutral and is not miscible with the crude oil, the bottle (5) may be devoid of the mobile wall (54) or the mobile membrane. Therefore, the physical separation between two compartments (6, 7) can be avoided. Such a configuration facilitates the construction of the used bottle (5) and can improve the precision of the pressure measurement.

The device according to the invention is implemented according to the transfer method of the sample of the invention, of the bottle (5) to the measuring cell (2).

After a first step, the bottle (5) is connected to the measuring cell (2) and the weighing member (10) at the sluice gate level (15, 16) placed on the duct (21) and at the sluice gate level (9) placed at the end of the duct (8).

The connection to the duct (21) is immobile (not represented), that allows connecting the sampling vessel (5) over other measuring device, particularly on a known measuring device of thermodynamic characteristics of a hydrocarbon, for example, over a known transitiometer.

After another step, the calibration of the balance is carried out (10) opening the sluice gates (9) and (12) in order to weigh the compression fluid that is at the same pressure that the crude oil sample. Weighing the compression fluid, with known density and controlling its pressure, it can be determined whether the initial conditions or the reservoir conditions (RC) are close to the bubble pressure. In this case, the use of samples whose pressure is close to the bubble pressure is avoided.

The comparison of the sample pressure in reservoir conditions (RC) and bubble pressure is carried out from measurements carried out previously from bibliographic data.

In a next step, the bottle (5) is heated up to a measuring temperature that is advantageously the reservoir temperature (RT). It is the temperature to which the oil sample was after its extraction.

The heating is carried out by known means as such. After obtaining the reservoir temperature (RT), the bottle (5) is maintained at temperature in the insulated enclosure (not represented) in a similar manner as maintaining the transitiometer temperature.

During the heating, the initial pressure of the sample in the bottle (5) is equally maintained constant in the sluice gate (9) allowing controlling the exit of the compression fluid, i.e. of mercury, out of the compartment (7) of the bottle (5).

Since the bottle (5) is connected without any possibility of circulation of the sample between the bottle (5) and the transitiometer, the temperature of the sample is maintained isolated from the scanning transitiometer.

Furthermore, the neutral liquid, of mercury, contained in the reservoir (R2) is at least introduced in the duct (25) opening the sluice gate (30) or advantageously in other ducts (21, 24) equally opening the other sluice gates.

During the filling of the circuit with mercury, care must be taken to evacuate the residual air present in the circuit. The mercury, eventually collected, during the air evacuation, for example at the sluice gate (31) level, is collected in a vessel (not represented) adapted for its reuse.

Once the circuit is filled with mercury, the sluice gate (30) is closed. The stability of the pressure is verified.

The absence of leakage can be also verified in the circuit before filling, injecting nitrogen in the circuit by means of a sluice gate (31). In this case the sluice gate (30) placed at the reservoir exit (R2) is closed during the injection of nitrogen to avoid any projection of mercury out of the reservoir (R2). All the circuit is pressurized with nitrogen during a given period, for example 30 minutes. Once the verification is carried out, the sluice gate (31) is closed and the residual nitrogen is evacuated, for example, by a discharge sluice gate (19).

Once the evacuation with nitrogen is carried out, the reservoir with nitrogen is disconnected from the sluice gate (31) and it is replaced with a vacuum pump (not represented) that, at least for fifteen minutes, ensures the draining of all the circuit. During the draining circuit, it is conveniently to verify that there is no leakage in the circuit. That is why the pressure is permanently controlled. After the draining, the sluice gate (31) is closed and the pump is disconnected from the circuit. The entire measuring device, i.e. the scanning transitiometer and the different ducts is also maintained in a vacuum of 0.13 MPa.

In the next step, the sluice gate (30) is progressively opened to transfer the mercury from the reservoir (R2) to the circuit up to the equilibrium, meanwhile the circuit is filled in with mercury. The filling is advantageously carried out by gravity, using the height difference between the circuit and the reservoir (R2) of the mercury. Furthermore, the reservoir (R2) of mercury must remain filled.

Alternatively, it is possible to use a pump (not represented) during this step.

When the mercury in the circuit is equilibrated in each point of the circuit, it is convenient to close all the sluice gates.

Shortly after this step, when the system is filled of mercury, it is pressurized. The sluice gate (26) is opened and the pump (28) is programmed, connected to the reservoir (R1) of mercury to increase the mercury pressure in the device up to the study pressure that is the pressure of the sample contained in the bottle (5) and that corresponds to the original pressure or reservoir pressure (RP).

In other terms, a reservoir (R2) of mercury serves to saturate the circuit in neutral liquid and another reservoir (R1) ensure the pressurization of a neutral liquid by a compression liquid.

In the alternative case when the neutral liquid and the compression liquid are the same and are made of mercury, it is possible to use a unique reservoir of mercury. The ducts and the circuit are now adapted to this particular configuration. Nevertheless, the presence of two reservoirs (R1, R2) facilitates the manipulations of mercury and improves security.

Once the pressure of study was attainted, the sluice gates (30) and (32) are open. The security sluice gate (16) placed on the conduct (21) connecting the bottle (5) to the transitiometer (2) is equally opened.

At this stage, preferably, the pressure is maintained constant in all communicated ducts, during at least 30 minutes in order to confirm the total absence of micro leakages as well as to ensure that the pressure is easily maintained.

The pressurization pump (28) of the circuit is a pump reversibly mounted between the sluice gates (26) and (27) in order to maintain constant the pressure prevailing in the circuit during the temperature set of this least. This pump (28) allows increasing or reducing pressure.

In a next step, the transitiometer (2) and the different ducts are heated at the measuring temperature that is the temperature of the bottle (5) or reservoir temperature (RT).

Once this step is carried out and the pump (28) is stopped, the elements of the scanning transitiometer and the bottle (5) are in barometric and thermal equilibrium.

Afterwards, the oil contained in the compartment (6) of the sampling bottle (5) is brought to a pressure superior to its initial pressure (PR). The interior pressure is increased (6) in order to obtain a difference of pressure allowing the transfer of the bottle sample (5) to the transitiometer (2) and allowing avoiding any risk of precipitation during the transfer, avoiding bringing closer the bubble pressure of the sample of the studied oil. After this step, the pressure is now increased from 5 MPa to 7 MPa related to the initial pressure, an increase of pressure, preferably close to 5 MPa.

The pressure increase is carried out by a pump (not represented), which is connected to a weighing member (10). This pump, compressing the compressing liquid, i.e. the mercury contained in the compartment (7) of the bottle (5), compresses the sample contained in the compartment (6) because of the displacement of the compressing liquid in direction of the compartment (6).

During the next step, once the overpressure of the sample is carried out, the sluice gate (15) is open. Because of the depression created, the sample is displaced from the bottle (5) up to the measuring cell (2).

The sluice gates (15), (16), (18), (19) being open, from the ducts of the circuit, particularly the duct (21), connecting the bottle (5) to the measuring cell (2) are capillaries and the bottle (5) has the height inferior to the height of the measuring cell (2), a displacement by gravity of the mercury column after it is transferred from the cell (2) to the bottle (5). Simultaneously, the oil sample is displaced from the bottle (5) to the measuring cell (2).

The sample now occupies a volume of the measuring cell (2) identical to the mercury volume.

In the absence of the mobile wall (54) in the bottle (5) and since its density is superior, the mercury directly displaces by gravity from the compartment (6) to the compartment (7) containing mercury as compressing liquid.

Alternatively, when the bottle (5) comprises a mobile wall (54), the mercury is deposited on this wall in the compartment (6), without mixing with the oil.

In equilibrium in the measuring cell (2), the oil sample has the measuring pressure (PR) that is the initial pressure that was in the bottle (5).

The crude oil volume introduced in the measuring cell (2) during the opening of the sluice gates (15) and (19) corresponds to the mercury volume displaced from the measuring cell (2) in the bottle (5).

Once the sample is transferred, the bottle (5) is isolated closing the sluice gates (15) and (16).

After the return to equilibrium, the oil volume displaced after weighing a quantity of mercury displaced by means of a weighing member (10) is determined. The initial pressure of the liquid present in the bottle (5) and the initial volume of this bottle (5) were not modified during the transfer of the sample.

Also, the difference of the mass corresponds to the mercury volume that replaced the sample volume of the oil in the bottle (5).

Therefore, from the mass of the mercury quantity introduced in the bottle (5) and knowing the density of the mercury, it is possible to calculate the volume of the mercury initially present in the measuring cell (2) that was displaced in the bottle (5). Now, the identical oil volume displaced from the bottle (5) and introduced into the measuring cell (2) is known.

This determination of the sample volume introduced in the transitiometer (2) is independently carried out from the initial volume of the sample in the bottle (5) maintaining its pressure (PR).

This determination can be easily repeated up to that moment when the bottle (5) does not contain more oil.

During the measurements carried out in the transitiometer (2), the bottle (5) is isolated from the measuring circuit closing the sluice gates. Advantageously, the bottle (5) is maintained at the same temperature and with slight suppression in order to facilitate the transfer of the sample during the following measurements.

Once the measurements are carried out, the heating of the bottle (5) is stopped and it must be left to rest offsetting the pressure drop, for example by means of a pump, for example a pump related to the weighing member (10). The bottle (5) is also maintained at its origin pressure until it is at room temperature. Once the room temperature is attained, the bottle (5) is isolated and is disconnected from the circuit closing the sluice gates (9), (15), (16).

Once the measurements were done, the transitiometer is cooled and is left at atmospheric pressure; the oil and the mercury present in the circuit are collected, for example by draining the sluice gate (31).

Example 2: Device and Method for Titration of Asphaltenes from the Crude Oil Samples—FIG. 2

In this second embodiment, the titration of the crude oil sample is carried out with an organic solvent. The titration method is also well known.

For this second embodiment, the transfer device of the sample is similar to the device from the Example 1 and the transfer of a known volume of sample is carried out according to method of the Example 1.

The determination of these new parameters implies the mounting on the circuit of a titration vial (35) between the sluice gate (19) and the sluice gate (36) provided on the duct (25). The sluice gate (19) is not a discharge sluice gate anymore.

The geometry of the duct (25) is different and needs a different configuration of the reservoir (R2) and the sluice gates (30), (31), (33).

The vial (35) is connected to the chamber (22) and the duct (25) provided with a three-way sluice gate (36) by means of a duct (37) is also provided with a sluice gate (38).

The vial (35) behaves similarly as the transitiometer from Example 1, the steps of transferring the sample are identical to those described for Example 1, particularly, the steps of heating the bottle (5) or of the filling with mercury of the circuit contained in the reservoir (R2). All the circuit is submitted to a pressure maintenance test taking the part containing the titration fluid to the study pressure similar to the first embodiment by closing and opening the sluice gates.

After causing a void in the circuit and before filling it in with mercury, the titration liquid is charged into the titration vial (35) now that it is isolated from the circuit by previous closing of the sluice gates (19) and (38).

Afterwards, the sluice gate (38) is opened in order to communicate the titration vial (35) and the circuit filled of mercury.

Then, the titration liquid is taken to the measuring pressure or reservoir pressure (PR).

After the pressure stability test was carried out in order to verify the absence of the leak, the transitiometer is, similarly to Example 1, brought to temperature and pressure conditions of the measurement.

By the known titration method, with the help of n-heptane, in measuring temperature and pressure conditions, complementary thermodynamic characteristics are obtained, allowing, with the data related to phase envelopes and bubble pressure, to reliably describe the thermodynamic behavior of the hydrocarbon during its extraction and its treatment. During this titration method, a determined quantity of alkane is added to the asphaltene crude oil sample implying now the precipitation of the asphaltenes that are separated by filtration and then are weighed allowing the determination of the concentration of asphaltenes in the crude oil sample.

Knowing the sample volume, the temperature and pressure of the reservoir, it allows determining the thermodynamic variables. Indeed, the three variables V, P, T are known, it is possible to maintain a constant variable and to follow the evolution of a second variable based on a third variable. Therefore, it is possible to obtain the following thermodynamic derivatives: dP/dV, dV/dP, dT/dV, dT/dP.

The invention claimed is:

1. A method for transferring under pressure a fluid from a deposit, by means of a sampling vessel wherein a fluid sample is maintained at a reservoir pressure (RP) and said method comprising the following steps:
   a) measuring by a measuring device, in the absence of contact with the fluid sample, the pressure of the fluid sample maintained at reservoir pressure (RP) in the sampling vessel;
   b) connecting the sampling vessel to the measuring device, maintained closed and at the reservoir pressure of the measuring device;
   c) filling the measuring device with a second neutral liquid fluid with a known density and greater than the density of the fluid from the deposit;
   d) increasing the pressure in the measuring device and the pressure of the second neutral liquid fluid, up to a pressure equal to the pressure of the fluid sample from the deposit determined during the step (a);
   e) increasing the pressure of the fluid sample from the deposit contained in the sampling vessel to a pressure greater than the pressure of the second neutral liquid fluid contained in the measuring device;
   f) transferring simultaneously, all or part, of the fluid sample from the deposit from the sampling vessel to a measuring cell, by balancing the pressures of the sampling vessel and the measuring cell; and a volume equivalent to the second neutral liquid fluid, of the measuring cell to the sampling vessel;
   g) disconnecting the sampling vessel, measuring the density of the second neutral liquid fluid transferred into the sampling vessel, to a constant pressure in the absence of contact with the fluid sample from the deposit; and
   h) calculating the volume of the sample of the fluid from the deposit, displaced and introduced in the measuring cell.

2. The method according to claim 1, wherein the fluid from the deposit is crude oil comprising an asphaltene phase.

3. The method according to claim 1, comprising step (e) for increasing the pressure of the sample extracted from the deposit contained in the sampling vessel up to a pressure greater than 5 MPa to 7 MPa of the pressure of the second neutral liquid fluid contained in the measuring device.

4. The method according to claim 1, comprising heating the fluid sample from the deposit in the sampling vessel or in the measuring cell at the reservoir temperature (RT) of the deposit.

5. A method for determining at least one thermodynamic characteristic of said fluid from the deposit comprising the transfer of a sample of the fluid from the deposit according to claim 1 and step (i) for determining at least one thermodynamic characteristic of the fluid extracted from the deposit by means of a measuring cell adapted to carry out the determination of at least one such thermodynamic characteristics.

6. The method according to claim 5, for determining at least one thermodynamic characteristics selected among a thermophysical or thermomechanic characteristic, a phase transition envelope, bubble pressure, titration, compressibility and thermal expansion.

7. The method according to claim 5, during which the thermodynamic characteristic is determined by a variation of a first parameter selected among pressure (P), temperature (T) or volume (V), based on a second parameter, maintaining constant a third parameter.

8. The method according to claim 1, comprising the implementation of
- one or various elements selected from the group consisting of probes, optical fibers or other means for connecting spectroscopic measure or analytical sensors and a plurality of said sensors, such as infrared sensors, ultra-violet spectroscopic sensors or mass spectroscopy sensors; or
- miniature capillaries or micro-capillaries and the injection of at least a fluid of an alkane (particularly pentane, hexane or heptane) or the injection of at least one fluid in a supercritical state selected from the group consisting of nitrogen in supercritical state, $CO_2$ in a supercritical state, and methane in a supercritical state; or
- an inside stirring system of the measuring cell.

9. A transfer device at a reservoir pressure (RP) of a sample of fluid extracted from a deposit comprising:
- a measuring device with thermodynamic characteristics comprising at least a measuring cell, a reference cell, heating devices and devices to increase or decrease the pressure in the measuring and reference cells;
- an immobile sampling vessel connected to said measuring cell, and comprising a compression liquid and placed at a height less than the height of the measuring cell;
- a first reservoir (R1) of a liquid and neutral compression fluid compared with the fluid sample extracted from the deposit, said first reservoir connected to said measuring cell;
- a means to increase the pressure in the sampling vessel;
- a pressure equilibrium device in the measuring cell and in the sampling vessel;
- a second reservoir (R2) of liquid and neutral fluid compared with the sample of fluid extracted from the deposit, said liquid and neutral fluid is placed at a height greater than the height of the first reservoir (R1) of the compression fluid, said second reservoir connected to said measuring cell; and
- ducts connecting the sampling vessel, the reservoirs (R1, R2) and the measuring cell.

10. The device according to claim 9, comprising a heating device of the sampling vessel.

11. The device according to claim 9, wherein the sampling vessel comprises
- a compartment connected by a duct to the measuring cell being able to receive the sample of the fluid extracted from the deposit and that will be transferred; and
- a compartment connected by a duct to a weighing member that is able to receive the compression liquid.

12. The device according to claim 9, wherein the sampling vessel comprises two compartments divided by a mobile wall in translation along a longitudinal axis (X) of the sampling vessel.

13. The device according to claim 9, wherein the measuring cell is a transitiometer.

14. The device according to claim 9, further comprising:
- one or various elements selected from the group consisting of probes, optical fibers or other devices for connecting spectroscopic measure or analytical sensors and a plurality of said sensors, such as infrared sensors, ultra-violet spectroscopic sensors or mass spectroscopy sensors; or
- miniature capillaries or micro-capillaries and the injection of at least a fluid of an alkane selected from the group consisting of pentane, hexane and heptane or the injection of at least one fluid in a supercritical state selected from the group consisting of nitrogen in supercritical state, $CO_2$ in a supercritical state and methane in a supercritical state; or
- an inside stirring system of the measuring cell.

15. The device according to claim 9, wherein the sampling vessel comprises a first compartment provided with an exit connected by a duct to the measuring cell and a second compartment provided with an exit connected by a duct to a weighing member.

16. The device according to claim 15, wherein the weighing member is connected by a duct only to a compartment of a compression liquid of the sampling vessel.

17. The device according to claim 9, wherein the neutral fluid and a compression fluid are identical.

18. The device according to claim 17, wherein the neutral fluid and the compression fluid are identical and are made of mercury.

19. The device according to claim 9, further comprising:
- a titration device of the fluid extracted from deposit;
- ducts connecting this titration device to the measuring device.

20. The device according to claim 19, wherein the titration device is a titration vial.

* * * * *